(12) United States Patent
Neumann-Raizel (10) Patent No.: US 12,298,321 B2
(45) Date of Patent: May 13, 2025

(54) DEVICES AND METHODS FOR PATCH CLAMP MEASUREMENT TECHNIQUES

(71) Applicant: Luigs & Neumann Feinmechanik und Elektrotechnik GmbH, Ratingen (DE)

(72) Inventor: Peter Neumann-Raizel, Ratingen (DE)

(73) Assignee: LUIGS & NEUMANN FEINMECHANIK UND ELEKTROTECHNIK GMBH, Ratingen (DE)

( * ) Notice: Subject to any disclaimer, the term of this patent is extended or adjusted under 35 U.S.C. 154(b) by 134 days.

(21) Appl. No.: 18/166,613

(22) Filed: Feb. 9, 2023

(65) Prior Publication Data

US 2023/0258666 A1 Aug. 17, 2023

(30) Foreign Application Priority Data

Feb. 16, 2022 (EP) .................................. 22157002

(51) Int. Cl.
*G01N 35/00* (2006.01)
*B08B 3/12* (2006.01)
*B08B 7/02* (2006.01)
*G01N 33/487* (2006.01)

(52) U.S. Cl.
CPC ......... *G01N 35/00623* (2013.01); *B08B 3/12* (2013.01); *B08B 7/028* (2013.01); *G01N 33/48728* (2013.01)

(58) Field of Classification Search
CPC ........ G01N 35/00623; G01N 33/48728; B08B 3/12; B08B 7/028; B08B 13/00; B01L 2300/0645; B01L 2400/0439; B01L 3/022; B01L 13/02
See application file for complete search history.

(56) References Cited

U.S. PATENT DOCUMENTS

| | | | |
|---|---|---|---|
| 4,861,332 A * | 8/1989 | Parisi .................. | A61F 9/00745 604/35 |
| 6,470,226 B1 | 10/2002 | Olesen et al. | |
| 2003/0022268 A1 * | 1/2003 | Lepple-Wienhues ....................... | G01N 33/48728 435/288.1 |
| 2004/0214312 A1 | 10/2004 | Tyvoll et al. | |
| 2017/0285152 A1 * | 10/2017 | Bao ....................... | B06B 1/0215 |
| 2021/0072223 A1 * | 3/2021 | Kolb ....................... | B01L 13/00 |

FOREIGN PATENT DOCUMENTS

| | | |
|---|---|---|
| CN | 211757274 U | 10/2020 |
| CN | 113663751 A | 11/2021 |
| EP | 1471352 A1 | 10/2004 |
| WO | 9850791 A1 | 11/1998 |
| WO | 2017027888 A1 | 2/2017 |

* cited by examiner

*Primary Examiner* — Akm Zakaria
(74) *Attorney, Agent, or Firm* — Abel Schillinger, LLP (57) ABSTRACT

Devices and methods for detecting one or more characteristics of cells with patch clamp electrodes, wherein the used patch clamp electrodes are cleaned by application of ultrasonic vibrations.

21 Claims, 2 Drawing Sheets

DEVICES AND METHODS FOR PATCH CLAMP MEASUREMENT TECHNIQUES

CROSS-REFERENCE TO RELATED APPLICATIONS

The present application claims priority under 35 U.S.C. § 119 of European Patent Application No. 22157002.1, filed Feb. 16, 2022, the entire disclosure of which is expressly incorporated by reference herein.

BACKGROUND OF THE INVENTION

1. Field of the Invention

The present invention relates to improved devices and methods for detecting one or more characteristics of cells with patch clamp electrodes, wherein the used patch clamp electrodes are cleaned by application of ultrasonic vibrations, and uses of the devices and methods.

2. Discussion of Background Information

In the patch clamp technique, the current flow through the individual ion channels in the cell membrane of a cell is measured. The current strengths are in the picoampere range. To measure these ion channels or the currents, an electrode with a very small aperture (approximately 1 µm) is placed on the cell membrane and the cell membrane is pulled a little way into the electrode by means of negative pressure so that an electrically tight connection is made between the glass edge and the cell membrane. After the measurements have been completed, part of the membrane usually remains on (or in) the electrode. With this contamination it is not possible to achieve a tight connection between the electrode and a new cell again. As a rule, the electrode is now exchanged for a new one. However, in automated systems or systems with higher measurement throughput, the electrode is not exchanged, but must be cleaned. Cleaning is done in the art by means of chemical solutions, such as cleaning solutions based on Alconox® products. The use of such or similar cleaning substances can be problematic because they often have a certain level of toxicity. Therefore, after treatment with cleaning solutions, the electrode must be rinsed. Despite the rinsing, however, traces of the cleaning agent can remain on the electrode which then can harm (or even kill) the cells to be examined and influence their behaviour, so that no reliable measurement results. As an example for the prior art EP 3 394 283 may be named.

Accordingly, there is still a lot of potential for improvement in the art.

In view of the foregoing, it would be advantageous to have available devices and methods for patch clamp measurement techniques that overcome at least some of the problems related with the devices and methods of the prior art and improve over those.

Particularly, it would be advantageous to have available devices and methods that are easier to employ than solutions known from the prior art.

Further particularly, it would be advantageous to be able to dispose of the necessity of using toxic cleaning agents.

In the present invention, if not specified otherwise, temperatures are given as degrees Celsius (° C.).

In the present invention, if not specified otherwise, operations are performed at environmental pressure (normal pressure/atmospheric pressure), i.e., at 101.3 kPa.

In the present invention, if not specified otherwise, the term "comprising" always also includes "consisting of", that is a respective list can, apart from those members mentioned also include other members (=comprise), or it can include only the mentioned members (=consist of) (in the latter case elements that are not important to the invention, like screws, cables and the like are not excluded).

SUMMARY OF THE INVENTION

In one aspect, the present invention provides a device for detecting one or more characteristics of biological, preferably living, cells comprising or consisting of: a chamber insertion tray into which at least one, preferably one, sample examination chamber and one or more cleaning chambers can be securely inserted, preferably at fixed locations; one or more, preferably 1 to 12, patch clamp electrodes, wherein the patch clamp electrodes are pipettes, each one having attached to its respective rear end (the end distant from the sample examination chamber) a pressure/vacuum port and an electrode holder with which the respective patch clamp electrode is held. The patch clamp electrodes can also be referred to as micropipettes or patch pipettes, as is known in the art.

The chambers that are used in the present invention can be pre-prepared, as the device of the present invention is intended to be modular, and can be inserted, removed and/or replaced depending on the desired purpose or necessities at any time (as long as not an actual measurement is conducted in/with that chamber). The chambers can be of various shapes and sizes but need to be able to be inserted to the insertion tray. They can have Petri dish-like shapes, bowl-like shape, cup-like shape, plate-like shape, or any other shape as long as sufficient room is present at its bottom for the necessary sample or the necessary amount of cleaning liquid; in some preferred embodiments the shape would resemble that of Petri dishes. In some preferred embodiments the chambers are indeed Petri dishes, whose lids are removed before taking measurements or cleaning action or other lidded vessels. Such configuration has the advantage that the sample or cleaning liquid can be protected as long as possible and is only subjected to the environment for as longs as absolutely needed (the lid can be replaced after measurements or cleaning). Alternatively, or additionally, the lids may also be provided with openings through which the electrodes/pipettes can be inserted in the chambers. The chambers can optionally be fixed in place with the insertion tray either via friction, if the sizes are closely matched to insertions/recesses in the tray or via fixation elements. These fixation elements can be magnets; particularly if the chambers are made of metal (which is also one possibility for also being the reference electrode—vide infra), screws, clamps, adhesives or the like.

Accordingly, the chamber insertion tray is configured such that it can hold at least one sample examination chamber and at least one cleaning chamber. The exact number of chambers it can hold (or actually holds, if it could hold more) is determined by the respective desires and/or necessities based on what kind and how many measurements should be done. The most basic chamber insertion tray in the context of the present invention would hold one examination chamber and one cleaning chamber. A further example would hold one examination chamber and two cleaning chamber, which might be (directly) adjacent to each other or lie on opposite sides with the examination chamber between them or at any desired angle between them (if the tray is considered a circle for this determination purpose).

One specific element of this embodiment is the fact that the device comprises one or more ultrasonic generation devices configured to provide ultrasonic vibrations to each of the one or more patch clamp electrodes.

It should be noted that the patch clamp technique in general is well known to the person skilled in the art and its fundamentals and working principle does not need to be explained her in detail.

In preferred embodiments of the present invention, the one or more ultrasonic generation devices are either attached to one or more, preferably all, of the electrode holders, or are attached to one or more, preferably all, of the cleaning chambers, or are both attached to one or more, preferably all of the electrode holders, and to one or more, preferably all, of the cleaning chambers.

The most preferred embodiment in this context is that the ultrasonic generation devices are either attached to one or more, preferably all, of the electrode holders, and are particularly integral part of the holders or holder structure.

In preferred embodiments of the present invention, the one or more ultrasonic generation devices are piezo-based ultrasonic generation devices, particularly piezo actuators. Such piezo actuators are based on crystals which change their outer dimension when a voltage is applied, as is known to the person skilled in the art. Piezo actuators can be used as all-ceramics and also, preferably multi-layer crystals.

Preferred multilayer piezo actuators than can be employed according to the present invention have operating voltages of from about −40 V to about 120 V, preferably from about −20 V to about 100 V, an operating temperature of from about −60° C. to about 200° C., preferably from about −40° C. to about 150° C.

While the exact sizes of the piezo actuators that can be employed according to the present invention can be chosen in dependence of the size of the entire device, which, in turn, depends on the exact usage, it is preferred in some embodiments if the actuators have a size of from 1×1×1 mm to 4×4×4 mm, particularly about 2×2×2 mm. These have preferably travel ranges of from about 1 μm to about 5 μm, more preferably from about 1.5 μm to about 3 μm, and particularly from about 2 μm to about 2.5 μm.

In some preferred embodiments, these actuators show an axial resonant frequency measured at 1 V(pp) of more than about 500 kHz, particularly more than about 600 kHz, and an electrical capacitance measured at 1V(pp), 1 kHz, RT of from about 15 nF to about 40 nF, preferably from about 20 nF to about 30 nF, particularly about 25 nF.

Particularly preferred actuators have all the mentioned features and properties in the most narrow ranges given.

For example, piezo actuators of the described kind that can be employed in the present invention are commercially available from PI (physics instruments).

In preferred embodiments of the present invention, the patch clamp electrodes have at their front end, which is the end with which they would contact the biological cell(s) in the sample examination chamber, have an apertured surface configured to be able to form a resistance seal with a membrane of a biological cell. That aperture surface usually is a round hole (as is usual for pipettes) having preferably a diameter of from about 0.5 μm to about 2 μm, preferably from about 0.8 μm to about 2 μm, further preferably from about 0.5 μm to about 1.5 μm, further preferably a diameter of from about 1.8 μm to about 1.2 μm, particularly preferred from about 0.9 μm to about 1.1 μm and especially about 1 μm, and a wall thickness of from about 0.05 μm to about 0.25 μm, preferably from about 0.1 μm to about 2 μm and particularly about 0.15 μm.

In preferred embodiments of the present invention, the device comprises a control device configured to provide control instructions at least to the patch clamp electrodes, preferably via the electrode holders, and/or to the ultrasonic generation devices. Of course, the control device can (be configured to) control more or even any of the functions of the device according to the invention.

In preferred embodiments of the present invention the control device is configured to, in the case of more than one ultrasonic generation devices, control the respective ultrasonic generation devices either synchronously or asynchronously.

The control device employed in the present invention preferably positions the patch clamp electrode (pipette) to the cleaning position using a positioning system. Ultrasound is active during the over- under- pressure sequence. The ultrasound frequency can be pre-set freely or controlled to achieve the best cleaning result. For example, during the cleaning of the pipette the transmission of light (UV, IR, visible) can be monitored and depending on that transmission the frequency and the duration of the application of the ultrasonic vibration be controlled depending on that.

Preferably, a previously programmed sequence with overpressure and under pressure runs parallel and is controlled by the control device. Duration, pressure strength and repetitions of the overpressure and under pressure can be programmed. After cleaning is completed, the patch clamp electrode (pipette) is repositioned to any desired position by control device.

Alternatively, though less preferred, in certain embodiments of the present invention, it is possible to control the functions manually.

In certain preferred embodiments of the present invention, the device of the present invention can be controlled by a microcontroller system with a dedicated software specifically designed and programmed for that purpose to create the ultrasound signal, trigger the over-/under pressure and the positioning.

One further specific embodiment of the present invention is a method for detecting one or more characteristics of biological, preferably living, cells comprising or consisting of the following steps:

A) providing a device, particularly a device according to the invention as described in more detail above and below, having at least one sample examination chamber;

B) providing the at least one sample examination chamber with a sample containing one or more biological cells in it, optionally in a nutrition medium;

C) contacting the sample with one or more clean patch clamp electrodes and measuring one or more characteristics via the patch clamp electrodes;

D) removing the one or more patch clamp electrodes from the sample and the sample examination chamber and moving the used one or more patch clamp electrodes to one or more cleaning chambers;

E) cleaning the one or more patch clamp electrodes in the one or more cleaning chambers;

F) optionally, after cleaning repeating steps C) to E), preferably with either the same sample or a new sample, using the cleaned one or more patch clamp electrodes.

It is a specific feature of this embodiment that the used one or more patch clamp electrodes are cleaned by transmitting ultrasonic vibrations to the used one or more patch clamp electrodes, optionally with the aid of the same physiological solution as the examination chamber containing the sample or with a non-toxic cleaning solution, which is particularly water, especially particularly deionised water; or the cleaning is done with the aid of the same physiological solution as the examination chamber containing the sample or with water, the latter of which can be tap water or deionized water.

In this context it is to be understood that a non-toxic solution should not harm, inhibit or suppress chemical reactions or electrophysiological responses from a single neuron. Many of the cleaning solutions used in the prior art in the concentrations they are used to clean electrodes/pipettes can be harmful or toxic to living cells.

Differently to that prior art, because of the use of ultrasound the device/system of the present invention is able to clean the patch clamp electrodes (pipettes) without such g solutions, preferably using only the solution of the bath (ACSF) or just water, particularly deionized water or tap water.

In preferred embodiments of the present invention the patch clamp electrodes are moved with the aid of a positioning device. While this can be in principle any positioning device known in the art for these or similar purposes, preferably an LN Junior Multipatch manipulator with an LN SM10 remote control system (LN being the company Luigs & Neumann GmbH) is used.

In preferred embodiments of the present invention the ultrasonic vibrations are transmitted to the used one or more patch clamp electrodes by applying ultrasonic vibrations via ultrasonic generation devices, attached to or being part of electrode holders attached to one or more, preferably all, of the patch clamp electrodes; or attached to one or more, preferably all, of the cleaning chambers, or attached to or being part of electrode holders attached to one or more, preferably all, of the patch clamp electrodes, and attached to one or more, preferably all, of the cleaning chambers.

Not the least, some aspects of the present invention provide the use of the device according the present invention or the method according to the present invention to detect one or more characteristics of biological, preferably living, cells.

Some further preferred embodiments according to the present invention and explanations are disclosed in the following:

It is one most preferred embodiment of the present invention that for the cleaning of the used one or more patch clamp electrodes only ultrasonic vibrations and optionally with the aid of the same physiological solution as the examination chamber containing the sample or with a non-toxic cleaning solution, particularly water, especially particularly deionised, water, are used, but no toxic cleaning compositions, in particular none comprising about 33-43% sodium bicarbonate, about 10-20% sodium (C10-C20) LAS, about 5-15% sodium tripolyphosphate, about 5-15% tetrasodium pyrophosphate, about 1-10% sodium carbonate and about 1-5% sodium alcohol sulfate.

According to the invention, due to the throughput requirements of performing electrophysiological measurements in tissue or cell cultures, a simple non-toxic cleaning procedure was developed to eliminate the need for pipette replacement or the need for toxic cleaning agents. The removal of biological material from the glass surface, as well as the use of non-toxic cleaning agents are main aspects. In this context, it is to be noted that due to the small aperture of the patch clamp electrodes, i.e., the pipettes, the application of overpressure and underpressure alone will not lead to a sufficient cleaning effect. According to the present invention this problem/insufficiency of the prior art was solved by applying ultrasonic vibrations to the patch clamp electrodes, i.e. the pipettes. Preferably this is done with the aid of piezo devices, particularly piezo actuators.

However, while they are preferred in most variants of the present invention, the invention is not restricted to the employment of piezo devices and other methods for generating ultrasonic vibrations are also envisioned by the present application.

When ultrasonic vibrations are applied to the patch clamp electrodes, i.e., the pipettes, the substances adhering to the surfaces of these, particularly cellular residues, are shaken loose and can easily be ejected from the patch clamp electrodes, i.e., the pipettes, by applying alternating over- and underpressure to them, optionally with the aid of water.

For the effect of the invention it is possible to apply the ultrasonic vibrations directly to the patch clamp electrodes, i.e., the pipettes, e.g. if the ultrasonic generating device is part of the electrode holder. However, in the context of the invention it is also possible to indirectly apply the ultrasonic vibrations, in that they are applied to the cleaning chamber, in which water is present and the patch clamp electrodes, i.e., the pipettes, are partly (with their front ends, i.e. tips) immersed in this water. The vibrations transmitted by the water are sufficient to achieve this cleaning effect, particularly, if the water is alternatingly sucked in and blown out of the patch clamp electrodes, i.e. the pipettes, by application of alternating under- and overpressure.

Of these possibilities the direct application of the ultrasonic vibration to the patch clamp electrodes, i.e. the pipettes, is preferred.

Because of the mechanical removal of the substances, particularly cellular residues, the utilization of a cleaning solution that dissolves or removes all these residues from the surfaces of the patch clamp electrodes, i.e., the pipettes, is not necessary anymore and can be disposed of. This means that only one simple cleaning chamber is needed (in which the patch clamp electrodes, i.e., the pipettes, are immersed (with their tips) into simple water), but not several different cleaning chamber/steps with different solutions or the like. Thus the solution of the present invention provides for an easier to conduct, easier to manufacture and cheaper solution than the prior art.

Additionally, the present invention is highly beneficial under ecological aspects as no toxic cleaning solutions are needed. However, in less preferred embodiments it is still possible to additionally employ cleaning solutions, if very specific, unusual situations occur, in which the ultrasonic/water cleaning effect is not sufficient—but this is not preferred.

In preferred embodiments of the present invention one or more piezo actuators are pressed against the outer surface of a patch clamp electrode, i.e., pipette, so that upon activation of the actuators, the actuators cause the patch clamp electrode, i.e., pipette, to swing by the application of a corresponding current impulse.

Frequency and amplitude can be adjustable or can be fixed. If there are several actuators, the control can be synchronous or asynchronous. The oscillation excitation of the electrode takes place during the cleaning process.

It is obvious and known to the person skilled in the art that the exact frequency that is applied to the patch clamp electrode (pipette) via the ultrasonic generation device is also dependant on the exact material and dimensions of the patch clamp electrode (pipette) and (to a lesser extent) the ambient conditions. If necessary, simple experiments can be done to evaluate which frequencies would be suited. The person skilled in the art is well aware of such.

In preferred embodiments of the present invention, two piezo actuators are used per patch clamp electrode, i.e., pipette.

In preferred embodiments of the present invention, the cleaning chamber is provided with the same physiological solution as the examination chamber containing the sample or with a non-toxic cleaning solution, particularly water.

In preferred embodiments of the present invention separate cleaning chambers are provided for each of the respective patch clamp electrodes, i.e., pipettes, which has the benefit that a contamination of one the patch clamp electrodes, i.e., pipettes, does not directly lead to a contamination of all the electrodes via a contaminated cleaning bath. Rather this enables the removal of one patch clamp electrodes, i.e., pipettes, from the process by cutting the current supply to it or simply not moving it back into the sample or the sample examination chamber—this means the process can be carried on, regardless, while without such compartmentalization it might have to be shut down entirely.

In preferred embodiments of the present invention, the device of the present invention also includes an additional bath electrode or reference electrode.

In other preferred embodiments of the present invention the examination chamber is configured to be the reference electrode, and is therefore made of a material that is electrically conductive, or the examination chamber has at least one electrically conducting part or section that acts as reference electrode.

Not the least, in one aspect the present invention is directed to a method for cleaning used patch clamp electrodes comprising or consisting of the steps
  a) providing a device having one or more cleaning chambers;
  d) removing one or more patch clamp electrodes from a sample and moving the used one or more patch clamp electrodes to the one or more cleaning chambers;
  e) cleaning the one or more patch clamp electrodes in the one or more cleaning chambers, wherein
  this method is also characterized in that the used one or more patch clamp electrodes are cleaned by transmitting ultrasonic vibrations to the used one or more patch clamp electrodes.

In preferred variants of this method according to the invention, the ultrasonic vibrations are transmitted to the used one or more patch clamp electrodes by applying ultrasonic vibrations via ultrasonic generation devices. These ultrasonic generation devices can, similarly as outlined above, be attached to or being part of electrode holders attached to one or more, preferably all, of the patch clamp electrodes and or to one or more, preferably all, of the cleaning chambers.

In further preferred variants of this method according to the invention, the cleaning with the ultrasonic vibrations is done with the aid of the same physiological solution as the examination chamber containing the sample or with a non-toxic cleaning solution, particularly water, especially particularly deionised, water. Further particularly the cleaning is done with the aid of the same physiological solution as the examination chamber containing the sample or with water, the latter of which can be tap water or deionized water.

In other words, the present invention can shortly be explained as follows: during a measurement with the device of the present invention, which can also be called a patch clamp recording, a patch clamp electrode, which basically is or can be a hollow glass tube (also known as a micropipette or patch pipette) filled with an electrolyte solution and a recording electrode connected to an amplifier, is brought into contact with the membrane of an isolated cell. Another electrode is placed in a bath surrounding the cell or tissue as a reference ground electrode (or the vessel of the bath itself is used as reference electrode). An electrical circuit can be formed between the recording and reference electrode with the cell of interest in between. During the establishment of the gigaohm sealing (gigaseal; resistance of the seal is equal to or more than 1 gigaohm) between the recording pipette and the cell membrane residuals of the tissue can stick to the surface. These residuals prevent a reuse of the electrode and have to be removed prior to any re-use. By the cleaning system of the present invention based on ultrasonic vibrations, these residuals can easily be removed and a re-use of the patch pipette is possible.

One advantage of the present invention is the fact that the outsides of the patch clamp electrodes (pipettes) do not need to be rinsed, while in systems according to the prior art they need to be as cleaning solutions adheres to the outsides and must be removed prior to reusing the electrode (pipette).

It may be one decisive advantage of the present invention that the dimensions of the system, regarding, inter alia, insertion tray, chambers, ultrasonic generation devices and pressure system, are scalable. By that the system can be easily customized to the respective demands of the scientist.

As the employed patch clamp electrodes (pipettes) those with usual sizes can be usually employed; to those the electrode holders are attached. As usual electrodes/pipettes can be used the device of the present invention can be adapted in its size to those, i.e., the device of the present invention can be similar in size to similar devices of the prior art—but the devices of the present invention can also be made smaller or larger, depending for instance on the size and number of electrodes/pipettes used.

It may be one decisive advantage of the present invention that the patch clamp electrodes are cleaned by transmitting ultrasonic vibrations and that the cleaning in this manner is very effective. When compared with the claiming methods according to the prior art, i.e., with a cleaning solution and cyclically application of under- and overpressure, the cleaning method according to the present invention often leads to better cleaning results than the prior art methods, even though no cleaning solution is used but also with just the ACSF (the same physiological solution as the examination chamber containing the sample) or with water, which does not need to be deionized.

The present invention can also be described compared with the prior art as follows: Normally, if an experimenter is trying to get a Gigaseal in a vital brain slice to record signals from one neuron, he has to perform countless recordings from different neurons to test connectivity and therefore, each time the experimenter needs to exchange the electrode to a fresh one to perform the next recording, because residuals from the slice and the performed Gigaseal remain on the tip of the electrode.

With the present invention it is possible to avoid the necessity of each time exchanging the electrode and instead it is possible and sufficient to clean the electrode by using ultrasound and over-/underpressure cycle. The electrode will be automatically moved to a bath, in some examples preferably filled with ACSF, and the cleaning cycle performed. Afterwards the electrode is moved (for example with an LN-Junior manipulator) back to the desired position. It is common in this field to use up to 12 electrodes at the same time. The addition of the ultrasound technology for cleaning the pipette according to the present invention, provides a seamless workflow and makes it easy to operate (and to operate recording). By that the possibility to perform from about 4 to about 8 or even up to 12 simultaneous patch recordings is increased by a huge scale. Therefore, the present invention enables one to get more data in a shorter time, which is crucial if one works with human brain slices.

The person skilled in the art can readily envision the exact configuration of the examination chamber, for instance size, wall thicknesses, materials etc. based on his general knowledge.

Where parts or the entire device are described as "consisting of", this is to be understood as referring to the essential components mentioned. Self-evident or inherent parts such as cables, screws etc. are not excluded. In particular, however, other essential components, such as further cleaning chambers or the like, which would change the function(s), are excluded.

The various embodiments of the present invention, e.g.—but not exclusively—those of the various dependent claims, can be combined with one another in any desired manner, provided that such combinations do not contradict one another.

BRIEF DESCRIPTION OF THE DRAWINGS

The present invention is now explained more fully with reference to the drawings.

In the drawings.

DETAILED DESCRIPTION OF EMBODIMENTS OF THE INVENTION

The drawings are not to be interpreted as limiting and are not to scale. The drawings are schematic and furthermore do not contain all the features that conventional devices have, but are reduced to the features that are essential for the present invention and its understanding, for example screws, connections etc. are not shown or not shown in detail.

Identical reference signs indicate identical or similar acting features in the drawings, the description and the claims.

Figure 1:
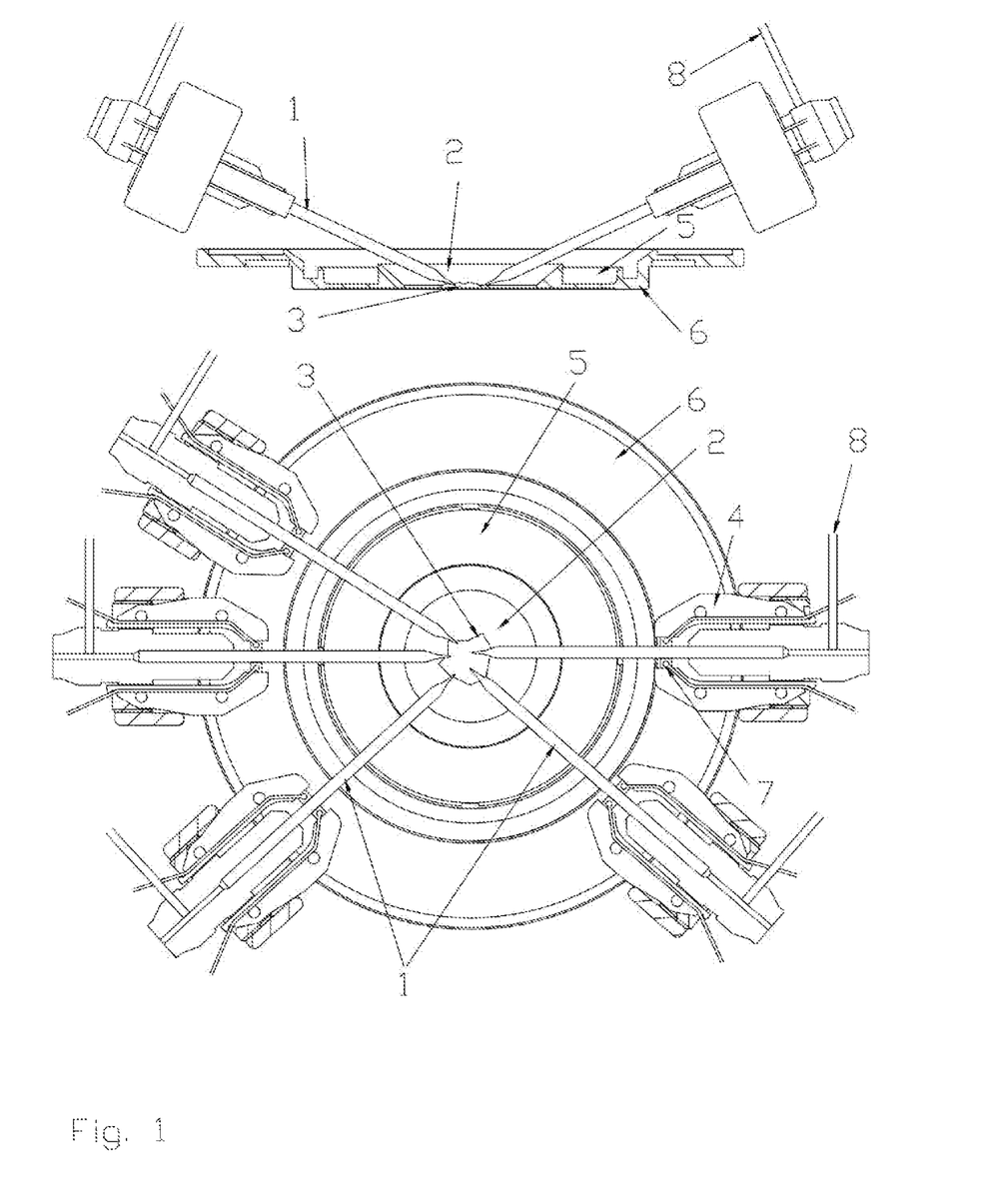
FIG. 1 is a highly schematic illustration of the device according to the present invention.

FIG. 1 shows highly schematic an illustration of the device according to the present invention. To this end, the figure is two-part, wherein the upper part is a sectional side-view and the lower part is a top-down view.

In the upper part two patch clamp electrodes, i.e. pipettes, 1 are shown, one left, one right, which both have their tips immersed in a sample 3 that has been provided in the sample examination chamber 2 of the device according to the invention. Additionally, it can be seen, that the patch clamp electrodes, i.e. pipettes, 1 have electrode holders 4 attached to their upper ends. While not visible in this perspective, the electrode holders 4 comprise ultrasonic vibration generation devices 7, particularly piezo-based ones, especially particularly piezo actuators. It can also be seen, that the sample examination chamber 2 and the at least one cleaning chamber 5 are arranged in the chamber insertion tray 6.

The lower part of FIG. 1 shows the same device according to the present invention in a top-down view. In this particular example, the device is based on a circular design, though this is not necessarily the case, but only one preferred embodiment. In this part of FIG. 1, five patch clamp electrodes, i.e., pipettes, 1 are illustrated, though more or fewer can be employed, preferably but not delimited to between 1 and 12. As can be seen these patch clamp electrodes, i.e., pipettes, 1 come into contact with different areas of the sample 3, so they provide for a more detailed measurement result than only one would. Due to the perspective of the lower part of FIG. 1, it is now possible to see that the electrode holders 4 actually comprise two ultrasonic vibration generating devices 7 per pipette 1 (the arrow pointing to the contact area with the tubular body of the pipette) in the shown embodiment. It is of course not necessary in all embodiments of the present invention that the electrode holder 4 has always two ultrasonic generation devices 7, in other embodiments there is only one ultrasonic generation device 7 per electrode holder 4, in other embodiments of the present invention there are three, four or even more. Additionally, each of the pipettes 1 has at least one pressure/vacuum port 8 with which overpressure and underpressure can be applied. Not shown in the drawings for clarity reasons are reference electrodes, which are also present during measurement.

While this figure shows a circular illustration with circular cleaning chamber 5, it is also possible to provide separate cleaning chambers 5 for each of the respective patch clamp electrodes, i.e., pipettes, 1.

Figure 2A:
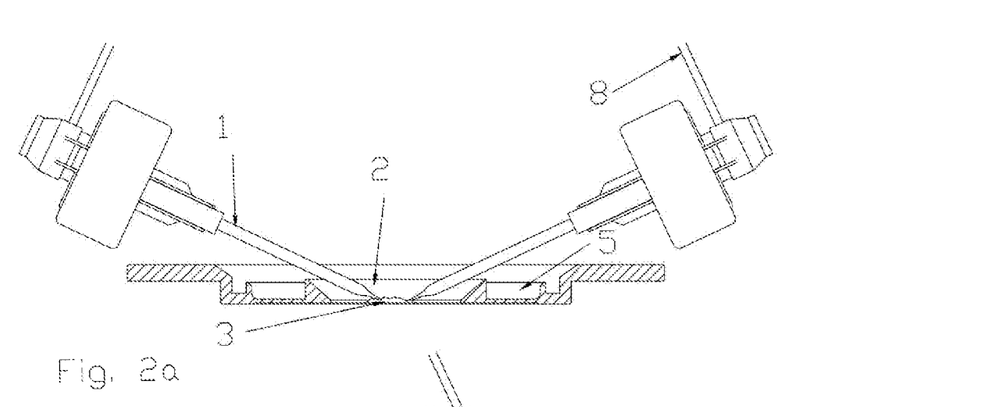
FIG. 2a shows the same upper part of the device shown in FIG. 1.
Figure 2B:
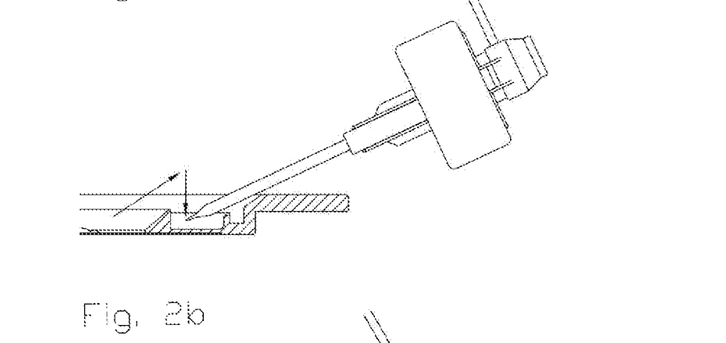
FIG. 2b shows the state after the measurements have been done.
Figure 2C:
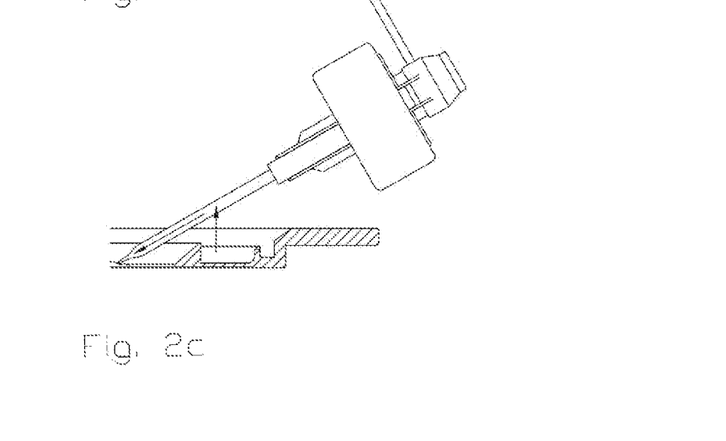
FIG. 2c shows the state after the cleaning of the patch clamp electrodes has been done.

FIG. 2 shows in its part 2a, 2b and 2c the three steps of measuring and cleaning according to the invention.

FIG. 2a is the same illustration as the upper part of FIG. 1. This shows the state in which measurements of the sample 3 are conducted, i.e., the patch clamp electrodes 1 are in contact with the sample 3.

FIG. 2b shows the state after the measurements have been done. The patch clamp electrodes 1 are being removed from the sample examination chamber 2 and are moved, along the path illustrated by the arrows into the cleaning chamber 5, in which the cleaning step is conducted.

FIG. 2c shows the state after the cleaning of the patch clamp electrodes 1 has been done. The patch clamp electrodes 1 are being removed from the cleaning chamber 5 and are moved conversely to FIG. 2b, along the path illustrated by the arrows into the sample examination chamber 2, in which a further examination/measurement step is conducted. It should be noted that the end position of the electrode can be programmed at any position along the shown path.

LIST OF REFERENCE SIGNS 1 patch clamp electrode
2 sample examination chamber
3 sample (containing one or more biological cells)
4 electrode holder with ultrasonic generation device, particularly piezo-based
cleaning chamber
6 chamber insertion tray
7 ultrasonic vibration generating device, particularly piezo-based
8 pressure/vacuum port The present invention is now further illustrated by the following, non-limiting examples.

EXAMPLE 1

In this example data is provided in Table 1 below (divided into three parts to better fit to pages) that was obtained upon measuring, inter alia, voltages of devices (electrodes/pipettes) according to the present invention.

Measurements were done with new pipettes as well as those after getting out of tissue but not being cleaned (AT/NC) as well as with pipettes that were cleaned with or without the aid of supersonic vibration provided with a piezo device during the cleaning process.

Cleaning was done is the same physiological solution as that in which the measurement was done.

The cleaning sequence in each case was 1 second with applied pressure and then 1 second without pressure. This sequence was repeated four times, and afterwards 1 second with applied pressure followed by atmospheric pressure.

| Vm (mV) | New (2) | AF/NC (3) | 1st cleaning (4) | AT/NC (6) | 2nd cleaning (7) |
|---|---|---|---|---|---|
| −100 | | | | −8.065 | −11.98 |
| −90 | | | | −6.5393 | −10.93 |
| −80 | | −6.82 | | −6.2749 | −9.858 |
| −70 | | −6.037 | | −5.573 | −8.368 |
| −60 | −6.809 | −5.208 | | −4.751 | −7.386 |
| −50 | −5.962 | −4.461 | −5.536 | −4.012 | −5.996 |
| −40 | −4.422 | −3.51 | −4.354 | −3.166 | −4.897 |
| −30 | −3.622 | −2.654 | −3.636 | −2.186 | −3.324 |
| −20 | −2.45 | −1.794 | −1.809 | −1.489 | −2.316 |
| −10 | −1.298 | −1.135 | −0.943 | −0.358 | −0.9785 |
| 0 | −0.277 | 0.083 | 0.47 | 0.627 | 0.04483 |
| 10 | 0.64 | 0.907 | 1.3042 | 0.992 | 0.9785 |
| 20 | 1.9898 | 1.9293 | 2.475 | 1.202 | 2.718 |
| 30 | 3.1566 | 2.979 | 3.9916 | 3.207 | 3.821 |
| 40 | 4.185 | 3.98 | 4.7498 | 4.267 | 4.854 |
| 50 | 5.68 | 5.135 | 5.908 | 4.977 | 6.799 |
| 60 | 6.731 | 5.863 | 7.109 | 6.287 | 7.868 |
| 70 | 7.344 | 7.232 | 7.784 | 7.387 | 9.457 |
| 80 | 8.569 | 8.382 | 9.291 | 8.687 | 10.44 |
| 90 | 9.985 | 9.572 | 10.36 | 9.447 | 12.04 |
| 100 | 12.512 | 10.575 | 11.532 | 11.017 | 13.46 |
| Slope from linear regression | 0.1147 | 0.09687 | 0.1134 | 0.09207 | 0.1268 |
| Resistance (in Mohm) | 8.71839582 | 10.3231135 | 8.818342152 | 10.8613012 | 7.886435331 |

| AT/NC (9) | 3rd cleaning(10) | 4th cleaning(11) | 3rd cleaning (5 s + pressure) (12) | new (1) |
|---|---|---|---|---|
| −4.804 | −9.114 | −8.613 | −8.888 | −9.51 |
| −4.661 | −8.411 | −7.808 | −8.398 | −9.035 |
| −4.135 | −7.454 | −7.207 | −7.216 | −7.772 |
| −3.95 | −6.562 | −6.48 | −6.231 | −7.287 |
| −3.331 | −5.437 | −5.463 | −5.373 | −6.353 |
| −2.665 | −4.661 | −4.438 | −4.894 | −4.894 |
| −2.118 | −3.597 | −3.574 | −3.628 | −4.283 |
| −1.425 | −2.826 | −2.62 | −2.6 | −3.099 |
| −1.15 | −1.77 | −1.826 | −1.699 | −1.874 |
| −0.3834 | −0.9615 | −0.7575 | 0.9393 | −1.295 |
| 0.1499 | −0.08811 | −0.01546 | −0.009275 | 0.2257 |
| 0.5859 | 1.031 | 0.7729 | 0.9661 | 0.9368 |
| 1.206 | 2.198 | 1.951 | 2.033 | 1.928 |
| 1.985 | 2.985 | 2.857 | 2.926 | 3.169 |
| 2.608 | 4.096 | 4.004 | 3.784 | 4.26 |
| 3.24 | 5.072 | 5.146 | 4.852 | 5.437 |
| 4.01 | 6.172 | 5.896 | 5.985 | 6.528 |
| 4.922 | 7.255 | 6.944 | 6.95 | 7.692 |
| 5.633 | 8.354 | 7.987 | 7.765 | 8.878 |
| 5.93 | 9.182 | 9.04 | 8.95 | 10.11 |
| 7.015 | 10.73 | 10.16 | 9.646 | 11.34 |
| 0.06002 | 0.09824 | 0.09439 | 0.09429 | 0.1053 |
| 16.661113 | 10.17915309 | 10.59434262 | 10.60557853 | 9.49667616 |

| AF/NC (2) | 1st cleaning (+piezo)(3) | AF/NC(5) | 2nd cleaning (−piezo) (6) | 3rd (+piezo)(7) |
|---|---|---|---|---|
| −6.944 | −9.94 | −7.633 | −7.967 | −9.303 |
| 6.273 | −8.966 | −7.04 | −7.36 | −8.488 |
| −5.597 | −7.908 | −6.346 | −6.571 | −7.707 |
| −4.95 | −7.114 | −5.604 | −5.832 | −6.7 |
| −4.288 | −6.142 | −4.903 | −5.166 | 5.964 |
| −3.597 | −5.24 | −4.134 | −4.299 | −5.032 |
| −2.925 | −4.248 | −3.3621 | −3.512 | −4.185 |
| −2.394 | −3.164 | −2.595 | −2.741 | −2.923 |
| −1.694 | −2.112 | −1.77 | −1.799 | −2.124 |
| −0.6338 | −1.071 | −0.895 | −0.9708 | −0.9507 |
| 0.01082 | 0.06183 | −0.05565 | −0.1314 | −0.17 |
| 0.7775 | 1.05 | 0.8548 | 1.023 | 0.6632 |

-continued

| | | | | |
|---|---|---|---|---|
| 1.546 | 2.096 | 1.795 | 1.844 | 2.221 |
| 2.364 | 3.285 | 2.742 | 2.854 | 2.886 |
| 3.209 | 4.378 | 3.741 | 3.899 | 4.016 |
| 4.096 | 5.614 | 4.777 | 4.971 | 5.579 |
| 4.991 | 6.781 | 5.814 | 6.038 | 6.781 |
| 5.883 | 8.031 | 6.921 | 7.187 | 7.87 |
| 6.874 | 9.164 | 8.057 | 8.31 | 9.233 |
| 7.86 | 10.5 | 9.201 | 9.501 | 10.38 |
| 8.854 | 11.68 | 10.39 | 10.74 | 11.7 |
| 0.07813 | 0.1073 | 0.0898 | 0.09328 | 0.1049 |
| 12.7991809 | 9.319664492 | 11.1358575 | 10.72041166 | 9.532888465 |

"New" indicates a new pipette.

In the measurement/cleaning of the second new pipette the step of 1 second plus pressure was replaced by 5 seconds plus pressure, each time.

It should be noted that the provided data is clear to the person skilled in the art, who would readily understand the data based on his experience with measuring/cleaning pipettes (albeit prior to the present invention cleaning was not done with ultrasonic vibrations).

As can be seen from the data, the cleaning of the devices according to the present with the process according to the invention provides for excellent cleaning without the need for additional cleaning solution.

Any documents cited in the application are incorporated by reference in their entirety, as long as their teaching does not contravene that of the present invention.

What is claimed is:

1. A device for detecting one or more characteristics of biological cells, wherein the device comprises:
   a chamber insertion tray into which at least one sample examination chamber and one or more cleaning chambers can be securely inserted;
   one or more patch clamp electrodes, each one having attached to its respective rear end a pressure/vacuum port and an electrode holder with which the respective patch clamp electrode is held; and
   one or more ultrasonic generation devices configured to provide ultrasonic vibrations to each of the one or more patch clamp electrodes,
   and wherein the one or more ultrasonic generation devices are
   attached to one or more of the electrode holders,
   attached to one or more of the cleaning chambers, or
   attached to one or more of the electrode holders, and to one or more of the cleaning chambers.

2. The device of claim 1, wherein the one or more ultrasonic generation devices are
   attached to one or more of the electrode holders.

3. The device of claim 1, wherein the one or more ultrasonic generation devices are
   attached to all of the electrode holders,
   attached to all of the cleaning chambers, or
   attached to all of the electrode holders and to all of the cleaning chambers.

4. The device of claim 1, wherein the one or more ultrasonic generation devices are piezo-based ultrasonic generation devices.

5. The device of claim 1, wherein the one or more ultrasonic generation devices are piezo actuators.

6. The device of claim 1, wherein the patch clamp electrodes at their front end have an apertured surface configured to be able to form a resistance seal with a membrane of a biological cell.

7. The device of claim 1, wherein the device further comprises a control device which is configured to provide control instructions at least to
   the patch clamp electrodes,
   and/or
   the ultrasonic generation devices.

8. The device of claim 1, wherein the device further comprises a control device which is configured to provide control instructions at least to
   the patch clamp electrodes via the electrode holders,
   and/or
   the ultrasonic generation devices.

9. The device of claim 7, wherein the control device is configured to, in the case of more than one ultrasonic generation device, control respective ultrasonic generation devices synchronously.

10. The device of claim 7, wherein the control device is configured to, in the case of more than one ultrasonic generation device, control respective ultrasonic generation devices asynchronously.

11. A method for detecting one or more characteristics of biological cells, wherein the method comprises:
    A) providing a device having at least one sample examination chamber;
    B) providing the at least one sample examination chamber with a sample containing one or more biological cells therein;
    C) contacting the at least one sample with one or more clean patch clamp electrodes measuring one or more characteristics via the patch clamp electrodes;
    D) removing the one or more patch clamp electrodes from the sample and the sample examination chamber and moving the used one or more patch clamp electrodes to one or more cleaning chambers;
    E) cleaning the one or more used patch clamp electrodes in the one or more cleaning chambers;
    the used one or more patch clamp electrodes being cleaned by transmitting ultrasonic vibrations to the used one or more patch clamp electrodes,
    and wherein ultrasonic vibrations are transmitted to the used one or more patch clamp electrodes by applying ultrasonic vibrations via ultrasonic generation devices which
      are attached to or are part of electrode holders attached to one or more of the patch clamp electrodes;
      are attached to one or more, preferably all, of the cleaning chambers, or
      are attached to or are part of electrode holders attached to one or more, of the patch clamp electrodes, and attached to one or more of the cleaning chambers.

12. The method of claim 11, wherein ultrasonic vibrations are transmitted to the used one or more patch clamp electrodes by applying ultrasonic vibrations via ultrasonic generation devices which are attached to or are part of electrode holders attached to one or more of the patch clamp electrodes.

13. The method of claim 11, wherein the cleaning with the ultrasonic vibrations is done with the aid of the same physiological solution as the examination chamber containing the sample or with a non-toxic cleaning solution, or the cleaning is done with the aid of the same physiological solution as the examination chamber containing the sample or with water, the latter of which is either tap water or deionized water.

14. The method of claim 11, wherein the cleaning with the ultrasonic vibrations is done with the aid of the same physiological solution as the examination chamber containing the sample or with deionized water, or the cleaning is done with the aid of the same physiological solution as the examination chamber containing the sample or with water, the latter of which is either tap water or deionized water.

15. A method for cleaning used patch clamp electrodes comprising or consisting of:
    a) providing a device having one or more cleaning chambers;
    b) removing one or more patch clamp electrodes from a sample and moving the used one or more patch clamp electrodes to the one or more cleaning chambers; and
    c) cleaning the one or more patch clamp electrodes in the one or more cleaning chambers;
the used one or more patch clamp electrodes being cleaned by transmitting ultrasonic vibrations to the used one or more patch clamp electrodes,
and wherein the ultrasonic vibrations are transmitted to the used one or more patch clamp electrodes by applying ultrasonic vibrations via ultrasonic generation devices which
    are attached to or are part of electrode holders attached to one or more of the patch clamp electrodes,
    are attached to one or more of the cleaning chambers, or
    are attached to or are part of electrode holders attached to one or more of the patch clamp electrodes, and attached to one or more of the cleaning chambers.

16. The method of claim 15, wherein the ultrasonic vibrations are transmitted to the used one or more patch clamp electrodes by applying ultrasonic vibrations via ultrasonic generation devices which
    are attached to or are part of electrode holders attached to one or more of the patch clamp electrodes.

17. The method of claim 15, wherein the cleaning with the ultrasonic vibrations is done with the aid of the same physiological solution as the examination chamber containing the sample or with a non-toxic cleaning solution, or the cleaning is done with the aid of the same physiological solution as the examination chamber containing the sample or with water, the latter of which is either tap water or deionized water.

18. The method of claim 15, wherein the cleaning with the ultrasonic vibrations is done with the aid of the same physiological solution as the examination chamber containing the sample or with deionized water, or the cleaning is done with the aid of the same physiological solution as the examination chamber containing the sample or with water, the latter of which is either tap water or deionized water.

19. A method of detecting one or more characteristics of biological cells, wherein the method comprises employing the device of claim 1.

20. The method of claim 19, wherein the cells are living cells.

21. The method of claim 11, wherein the method further comprises, after the cleaning of E):
    F) repeating C) to E) with the same sample or with a new sample, using the cleaned one or more patch clamp electrodes.

* * * * *